(12) United States Patent
Rochetin

(10) Patent No.: US 7,468,077 B2
(45) Date of Patent: Dec. 23, 2008

(54) PATELLAR RETRACTOR AND METHOD OF SURGICAL PROCEDURE ON KNEE

(75) Inventor: Olivier Rochetin, Meylan (FR)

(73) Assignee: Tornier SAS, Saint Ismier (FR)

( * ) Notice: Subject to any disclaimer, the term of this patent is extended or adjusted under 35 U.S.C. 154(b) by 538 days.

(21) Appl. No.: 11/194,452

(22) Filed: Aug. 2, 2005

(65) Prior Publication Data
US 2007/0043265 A1 Feb. 22, 2007

(51) Int. Cl.
*A61F 2/38* (2006.01)

(52) U.S. Cl. ..................... 623/20.3; 600/229

(58) Field of Classification Search ......... 600/210–211, 600/229, 235; 623/20.3, 20.31, 20.18, 20.19
See application file for complete search history.

(56) References Cited

U.S. PATENT DOCUMENTS

| | | | |
|---|---|---|---|
| 5,171,289 A | 12/1992 | Tornier | |
| 5,217,463 A * | 6/1993 | Mikhail | 606/88 |
| 5,314,485 A | 5/1994 | Judet | |
| 5,326,359 A | 7/1994 | Oudard | |
| 5,358,526 A | 10/1994 | Tornier | |
| 5,380,331 A | 1/1995 | Mikhail | |
| 5,405,399 A | 4/1995 | Tornier | |
| 5,429,639 A | 7/1995 | Judet | |
| 5,458,650 A | 10/1995 | Carrett et al. | |
| 5,505,731 A | 4/1996 | Tornier | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,766,256 A | 6/1998 | Oudard et al. | |
| 5,824,106 A | 10/1998 | Fournol | |
| 5,879,395 A | 3/1999 | Tornier et al. | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,206,925 B1 | 3/2001 | Tornier | |

(Continued)

OTHER PUBLICATIONS

Canale, S. Terry; "Campbell's Operative Orthopaedics" 2003, Mosby, vol. Three, Third Edition, pp. 2815-2816.*

(Continued)

*Primary Examiner*—Eduardo C Robert
*Assistant Examiner*—Elana B Fisher
(74) *Attorney, Agent, or Firm*—Faegre & Benson LLP

(57) ABSTRACT

The distal end part of the retractor according to the invention is provided both with terminal tips for abutment on one of the femoral condylar walls which define therebetween the intercondylar space, and with a wing extending laterally in projection from this end part in order to form a frontal surface for thrust, in a medial-lateral direction, of that part of the quadriceps muscle tendon containing the patella when the tips are in abutment in the intercondylar space. By using this retractor as a lever, the wing efficiently reclines the patella, without turning it completely on itself, entirely exposing one of the femoral condyles. This invention is more particularly applicable to a surgical procedure for implanting a unicompartmental knee prosthesis.

8 Claims, 8 Drawing Sheets

U.S. PATENT DOCUMENTS

| | | | |
|---|---|---|---|
| 6,299,646 B1 | 10/2001 | Chambat et al. |
| 6,328,758 B1 | 12/2001 | Tornier et al. |
| 6,334,874 B1 | 1/2002 | Tornier et al. |
| 6,379,387 B1 | 4/2002 | Tornier |
| 6,454,809 B1 | 9/2002 | Tornier |
| 6,488,712 B1 | 12/2002 | Tornier et al. |
| 6,540,770 B1 | 4/2003 | Tornier et al. |
| 6,582,469 B1 | 6/2003 | Tornier |
| 6,599,295 B1 | 7/2003 | Tornier et al. |
| 6,626,946 B1 | 9/2003 | Walch et al. |
| 6,761,740 B2 | 7/2004 | Tornier |
| 6,767,368 B2 | 7/2004 | Tornier |
| 6,802,864 B2 | 10/2004 | Tornier |
| 6,824,567 B2 | 11/2004 | Tornier et al. |
| 6,890,357 B2 | 5/2005 | Tornier |
| 6,969,406 B2 | 11/2005 | Tornier |
| 7,033,396 B2 | 4/2006 | Tornier |
| 2003/0009170 A1 | 1/2003 | Tornier |
| 2003/0009171 A1 | 1/2003 | Tornier |
| 2003/0028198 A1 | 2/2003 | Tornier et al. |
| 2004/0134821 A1 | 7/2004 | Tornier |
| 2004/0210220 A1 | 10/2004 | Tornier |
| 2004/0215200 A1 | 10/2004 | Tornier et al. |
| 2004/0230197 A1 | 11/2004 | Tornier et al. |
| 2005/0049709 A1 | 3/2005 | Tornier |
| 2005/0055102 A1 | 3/2005 | Tornier et al. |
| 2005/0165490 A1 | 7/2005 | Tornier |
| 2005/0203536 A1 | 9/2005 | Laffargue et al. |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288791 A1 | 12/2005 | Tornier et al. |
| 2006/0015185 A1 | 1/2006 | Chambat et al. |
| 2006/0173457 A1 | 8/2006 | Tornier |
| 2006/0235538 A1 | 10/2006 | Rochetin et al. |

OTHER PUBLICATIONS

Ratron et al., U.S. Appl. No. 11/626,735, entitled "Surgical Instrumentation Kit for Inserting an Ankle Prosthesis", filed Jan. 24, 2007.

Rochetin et al., U.S. Appl. No. 11/401,415, entitled "Surgical Apparatus for Implantation of a Partial or Total Knee Prosthesis," filed Apr. 11, 2006.

Rochetin, U.S. Appl. No. 11/670,274, entitled "Offset Stem Tibial Implantation," filed Feb. 1, 2007.

* cited by examiner

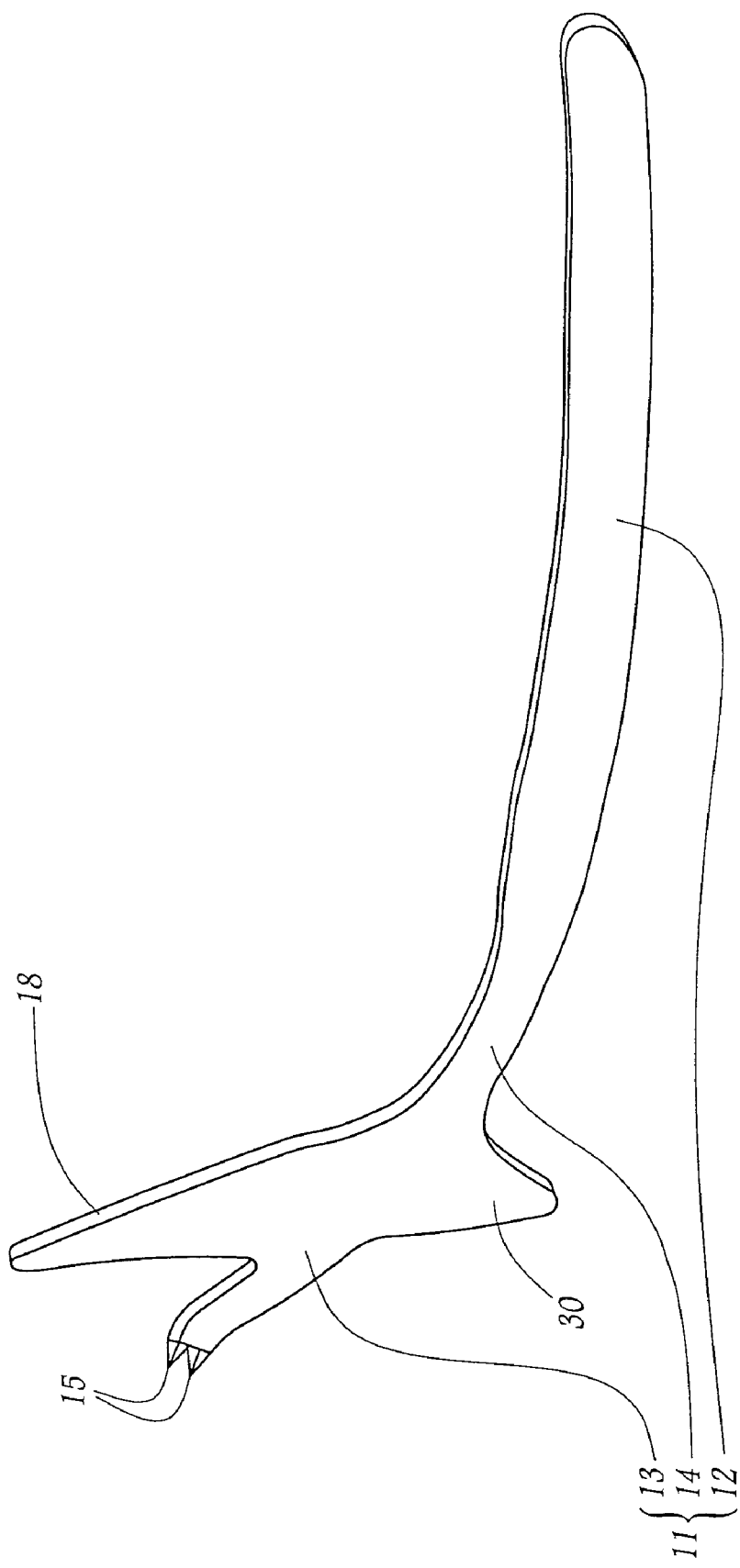

PATELLAR RETRACTOR AND METHOD OF SURGICAL PROCEDURE ON KNEE

FIELD OF THE INVENTION

The present invention relates to a patellar retractor intended to be used when performing knee surgery, particularly when a unicompartmental knee prosthesis is being implanted. The invention also relates to a method of surgical procedure on the knee employing such a retractor.

BACKGROUND OF THE INVENTION

When implanting a knee prosthesis, it is necessary to incise the anterior face of the knee and to recline the corresponding soft parts, i.e. disengage these soft parts rearwardly so as to render the operative field more visible and thus allow the surgeon to access the femoral and tibial epiphyses articulated on each other, particularly the femoral condyles and corresponding tibial articular cavities.

U.S. Pat. No. 5,380,331 discloses using various retractors intended to facilitate access and treatment of osseous or ligamentary zones of the knee operated on, depending on the stage of operation underway. This type of retractor is in the form of an elongated rigid body of which the distal end is introduced at the level of precise interstitial zones of the knee in order to raise, hold back and/or disengage muscular, osseous or ligamentary parts of the knee. U.S. Pat. No. 5,380, 331 thus envisages retractors of the tibia, the posterior ligament, the collateral ligament, etc. as well as patellar retractors of which the distal end, inclined with respect to the rest of the rectilinear body of the retractor, is applied against the outer lateral face of the tibial epiphysis in order to hook on the lower part of the quadriceps muscle tendon and dislocate the patella contained in the upper part of this tendon. Such patellar retractors prove in practice to be inefficient insofar as, by elasticity of the quadriceps muscle tendon, the patella tends to resume its initial place such that only a small extent of the lower zone of the tendon is efficiently disengaged towards one of the lateral sides of the knee. The surgeon is in that case often obliged to use these patellar retractors to force on the quadriceps muscle tendon and completely turn the patella round, risking damage to the tendon and/or the patella. In addition, as these patellar retractors abut against the outer lateral face of the tibia, their use requires a long and deep incision of the soft parts of the knee, even if the purpose of the operation is to implant a unicompartmental prosthesis, i.e. a prosthesis to be implanted only on one of the external or internal sides of the knee.

In the domain of implanting unicompartmental knee prostheses, intramedullary patellar retractors are known whose distal end is in the form of a rod and is to be introduced in the medullary cavity of the femur, after having previously bored an access to the cavity through the femoral epiphysis. Although, in practice this type of retractor limits the stress of the quadriceps muscle tendon and of the patella during reclination of the patella, the necessity of accessing the femoral medullar cavity leads to a long operation, which destroys the patient's osseous matter and is particularly invasive.

It is an object of the present invention to propose a patellar retractor which makes it possible to recline the patella efficiently without everting it, i.e. without turning it completely on itself, in order to offer the surgeon a good field of vision for the operation, while limiting the extent and depth of the incision necessary for use thereof, in particular which does not necessitate accessing the medullary cavity of the femur or of the tibia, and which is thus more particularly adapted to the implantation of a unicompartmental prosthesis.

SUMMARY OF THE INVENTION

To that end, the invention relates to a patellar retractor, including a globally elongated body, characterized in that the distal end part of the body is provided both with at least one terminal tip for abutment on one of the femoral condylar walls which define therebetween the femoral intercondylar space of the knee, and with a wing extending laterally in projection from this end part in order to form a frontal surface for thrust, in a medial-lateral direction, of the part of the quadriceps muscle tendon containing the patella when each tip is in abutment in the intercondylar space.

The quadriceps muscle tendon contains the patella insofar as the patella is integrated with the tendon.

The structure of the retractor according to the invention is particularly simple to manufacture and to use. When the surgeon seeks access to one of the femoral condyles, in particular to implant at that level a unicompartmental prosthesis, he inserts the distal end part of the retractor in the femoral intercondylar space, then, by causing each tip to abut on the wall of the treated condyle facing the intercondylar space, he makes a lever with the body of the retractor in order, using the lateral wing, to dislocate the patella by pushing it in a medial-lateral direction directed towards the other condyle. This simple gesture allows the surgeon to recline the quadriceps muscle tendon efficiently, by stressing the latter at the level of its current part, i.e. its part containing the patella, and using the lateral wing from which the frontal surface extends along the current part of the tendon. It will be understood that, in the invention, the term "tip" is understood broadly as a swelling or an element in relief, able to allow a stable abutment of the distal end of the retractor in the intercondylar space during its stress as lever for thrusting the patella.

As the stress of the quadriceps muscle tendon is applied over a substantial length of the current part of the tendon, no traumatic excess pressure or strain is applied to the tendon, while guaranteeing a sufficient lateral disengagement of the patella without having to turn it completely on itself. During the subsequent steps of the surgical procedure, particularly during osseous cuts of the condyle to be treated, the lateral wing of the retractor efficiently holds the patella in its reclined position while protecting it from the ancillary instruments used at the level of the treated condyle, for example cutting tools, since the wing is in that case interposed in the medial-lateral direction between the front zone of the treated condyle and the current part of the quadriceps muscle tendon. As the patellar retractor is advantageously manipulated in one hand, the operating gesture is simple and easily reproducible.

As the distal end of the retractor according to the invention may access the intercondylar space by passing through the incision necessary for access to the condyle to be treated, the use of the retractor does not involve any extension of the incision, the surgical approach in that case being able to be considered as mini-invasive. Moreover, no removal of osseous matter is necessary in order to use this retractor.

According to other advantageous characteristics of the retractor, taken separately or in any technically possible combinations:

each tip extends longitudinally in line with the distal end part;
  in longitudinal section, the or each tip, on the one hand, and the zone of the distal end part connected with the rest of the body, on the other hand, having respective opposite curvatures;

the frontal thrust surface is concave;

in frontal view, the wing presents a globally triangular contour of which one of the edges corresponds to the side of the distal end part from which the wing extends;

a second edge of the triangular contour, facing towards each tip, presents a hollowed profile, advantageously corresponding to an arc of circle of which the centre is located in the vicinity of each tip;

a third edge of the triangular contour, facing opposite each tip, presents a convex profile directed opposite the distal end part;

the proximal end part of the body forms or is provided with a handle for manually manipulating the retractor;

in longitudinal section, the profiles of the two end parts, except at the level of each tip, together form a substantially continuous arc;

the distal end part is further provided with a second wing extending in lateral projection from the end part, on the side opposite that from which the first wing extends.

The invention also proposes a method of surgical procedure on the knee which allows the patella to be efficiently reclined without turning completely on itself in order to offer a wide field of vision for the operation, while limiting the extent and depth of the necessary incisions or the like, in particular which does not necessitate accessing the medullary cavity of the femur or of the tibia.

To that end, the invention relates to a method of surgical procedure on the knee which includes the following successive steps of:

introducing a pointed distal end of a patellar retractor into the femoral intercondylar space, passing via the incision, and using the retractor as lever to dislocate the patella by pushing that part of the quadriceps muscle tendon containing the patella in a medial-lateral direction towards the other condyle, causing the pointed end to abut on the wall of the revealed condyle facing the intercondylar space.

The method according to the invention leads to accosting one of the external or internal condyles of the femur in a mini-invasive manner, since the patellar retractor used, by passing through the incision necessary for access to the condyle in order to treat it, involves no extension of the incision. The method according to the invention is thus more particularly adapted to the implantation of a unicompartmental knee prosthesis.

In practice, the patellar retractor as defined hereinabove is advantageously used when carrying out the method according to the invention.

According to other advantageous characteristics of this method:

in order to introduce the pointed end of the retractor in the intercondylar space, the pointed end is made to slide successively against the front wall and the wall turned towards the intercondylar space of the revealed condyle;

when the part of the quadriceps muscle tendon containing the patella is pushed, the patella is slid laterally on the anterior face of the lower epiphysis of the femur; and/or when the part of the quadriceps muscle tendon containing the patella is pushed, the posterior face of the patella is maintained directed towards the femur.

BRIEF DESCRIPTION OF THE DRAWINGS

The invention will be more readily understood on reading the following description given solely by way of example and made with reference to the accompanying drawings, in which:

FIG. 9 is a view in perspective of a variant patellar retractor according to the invention.

DESCRIPTION OF PREFERRED EMBODIMENTS

Figure 1:
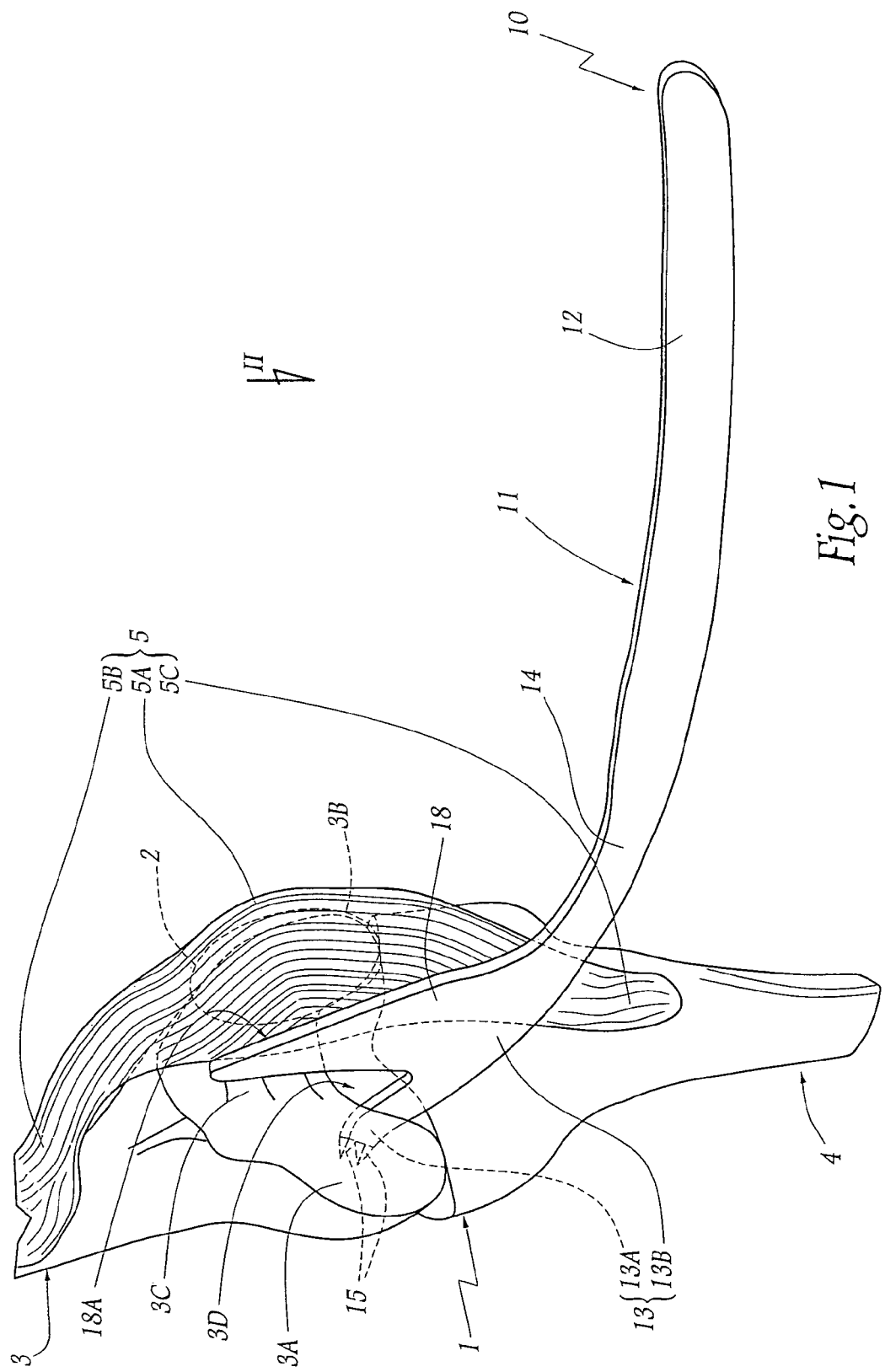
FIG. 1 is a view in perspective of a patellar retractor according to the invention, illustrated in the course of being used on a knee shown solely schematically.
Figure 2:
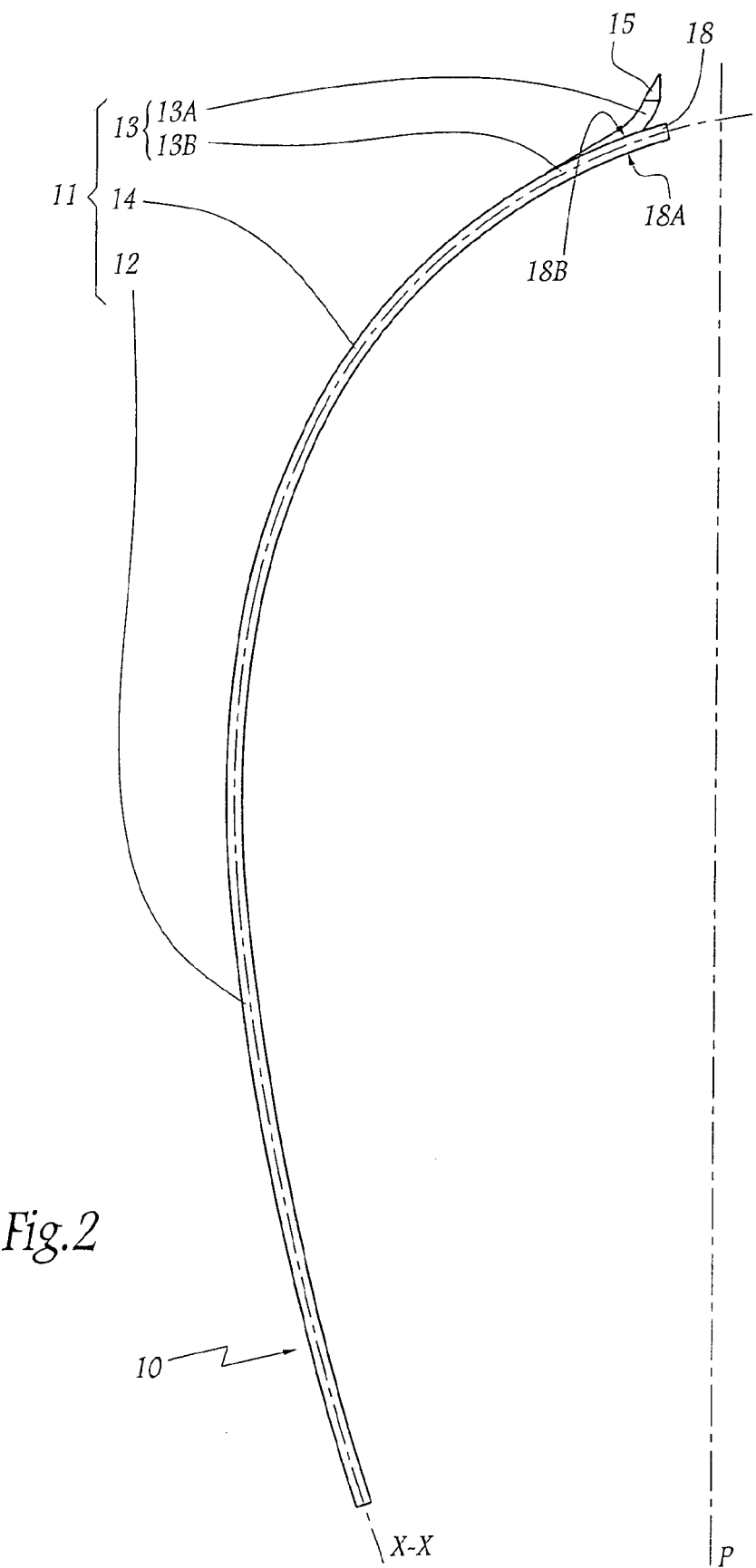
FIG. 2 is a view in elevation of the retractor, in the direction of arrow II of FIG. 1.
Figure 3:
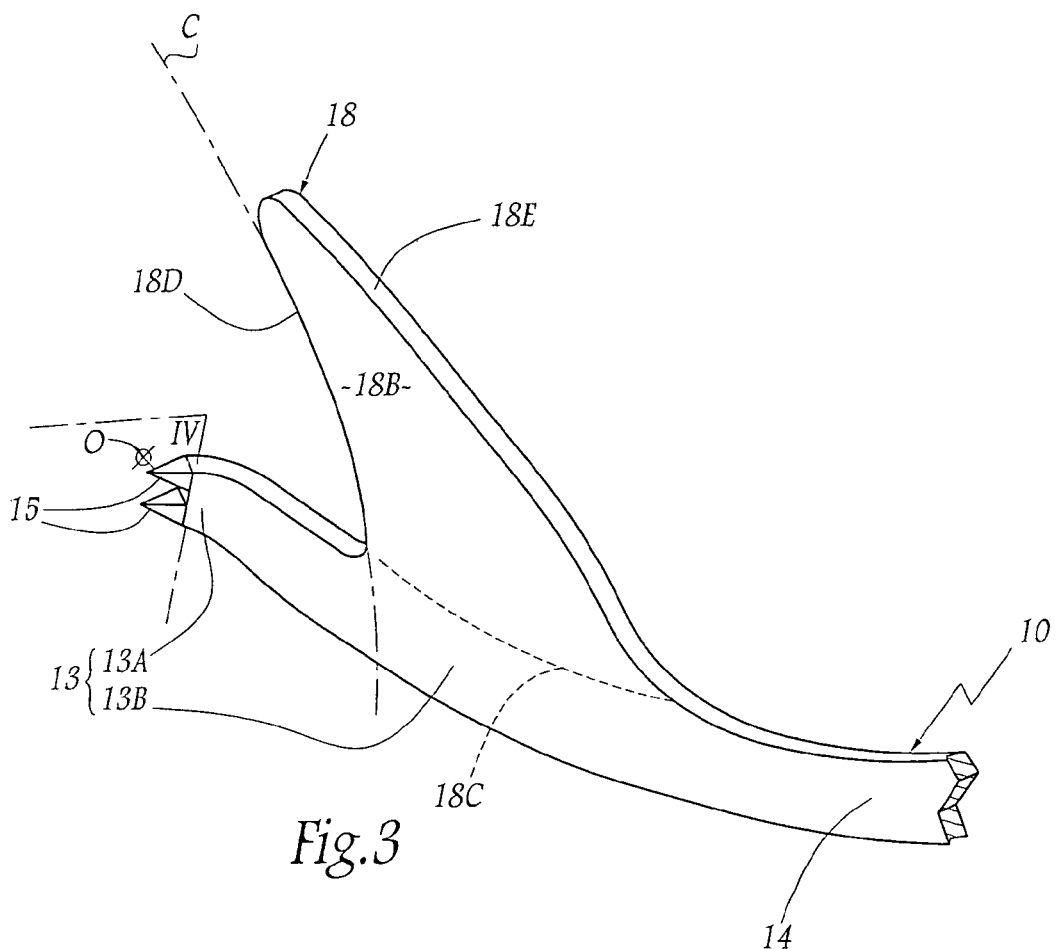
FIG. 3 is a view in perspective, on a larger scale, of the distal end of the retractor of FIG. 1.
Figure 4:
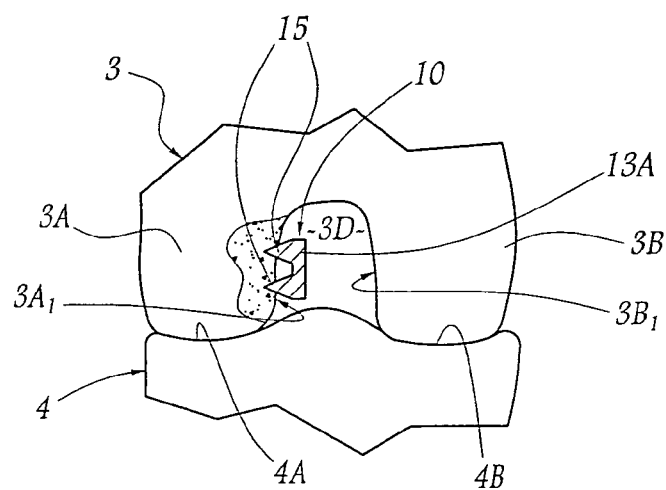
FIG. 4 is a schematic section, along plane IV of FIG. 3, of the retractor and of the corresponding osseous parts of the knee in the configuration of use of FIG. 1.

Referring now to the drawings, FIGS. 1 to 4 show a patellar retractor 10 adapted to recline the patella 2 of a knee 1. In FIGS. 1 and 4, the knee 1 is shown bent, with the lower epiphysis of the femur 3, the upper epiphysis of the tibia 4 and the tendon of the quadriceps muscle 5 which, to the rear of its current part 5A, contains the patella 2, while its upper (5B) and lower (5C) ends are respectively connected to the front faces of the femur 3 and of the tibia 4. The knee 1 shown being a right-hand knee, the femoral epiphysis includes an external condyle 3A and an internal condyle 3B, the upper parts of the condyles 3A and 3B being connected by an osseous trochlea 3C while, in their lower part, the condyles 3A and 3B are distant from each other in a medial-lateral direction, defining therebetween an intercondylar space 3D, clearly visible in FIG. 4. During the movements of the knee 1, the condyles 3A and 3B are articulated in complementary cavities 4A and 4B provided at the upper end of the epiphysis of the tibia 4.

The retractor 10 is constituted by a one-piece rigid body 11 made for example of metal or any material sufficiently rigid to hold the patella 2 back when the retractor is used, as described in detail hereinbelow. The body 11 is in the form of a piece elongated in a curved direction X-X, the other two dimensions of the piece being clearly less than its length. In other words, the body 11 is in the form of a curved, flat bar. The thickness of the body 11, i.e. its dimensions seen in plan view in FIG. 2, is substantially constant over the whole of its length, while its width varies as detailed hereinbelow.

The body 11 comprises a proximal end part 12 which forms a handle for manually manipulating it.

Opposite, the body 11 comprises a distal end part 13 connected to proximal part 12 by a current part 14 of the body, whose width increases from distal end part 13 to proximal part 12. Along axis X-X, the parts 12 and 14, as well as part 13 except for its distal terminal zone 13A, are each curved in the same direction and join one another in tangential manner, with the result that most of the body 11 presents, in longitudinal section, a continuous arcuate profile.

At its distal end part 13, the terminal zone 13A of the distal end part 13 is provided with two tips 15 which extend globally longitudinally in line with the part 13, the pointed end of each of these tips 15 constituting the distal terminal point of the retractor 10.

Each tip 15 is intended to abut firmly against the walls $3A_1$ and $3B_1$ of the condyles 3A, 3B, which delimit therebetween the intercondylar space 3D, as shown in FIG. 4. To allow the insertion of the distal end part 13 of the retractor 10 in the intercondylar space 3D, the thickness of the tips 15 and that of at least the terminal zone 13A are less than the medial-lateral dimension of the intercondylar space 3D, while the width of the terminal zone 13A is less than the vertical dimension of the intercondylar space 3D considered with the knee bent.

The tips 15 are connected to distal end part 13 in a curved manner. As shown in FIG. 2, the tips and the terminal zone 13A do not, however, extend in a direction joining the direction X-X without change of curvature but, on the contrary, in longitudinal section of the retractor 10, the tips 15 and the terminal zone 13A, on the one hand, and the rest 13B of the distal end part 13, i.e. the zone of distal end part 13 facing the parts 12 and 14, on the other hand, present respective opposite curvatures. In this way, on a frontal side of the body 11 seen in the direction of observation of FIG. 2, the part 13 presents a concave face at the level of its terminal zone 13A then convex at the level of its zone 13B, while, on the other side, it presents a convex frontal face at the level of its terminal zone 13A then concave at the level of its zone 13B.

The zone 13B of the distal end part 13 is provided with a solid wing 18 rigidly connected to the rest of the body 11, being for example integral with the body 11. The wing 18 extends the zone 13B laterally in projection from the longitudinal edge 13C of the zone 13B facing upwardly in operation. The wing 18 presents a substantially constant thickness, equal to that of the body 11 and, along axis X-X, a curvature identical to that of zone 13B, as is visible in FIG. 2.

Consequently, at the level of the two frontal sides of the wing 18 seen in the direction of observation of FIG. 2, the wing 18 respectively makes a concave surface 18A and an opposite, convex surface 18B. In practice, the curvature of the concave face 18A is dimensioned to correspond substantially to the geometry of the lateral flanks of the current part 5A of the tendon of the quadriceps muscle 5.

Seen frontally, the wing 18 presents a globally triangular shape of which one of the edges, indicated in broken lines in FIG. 3 and referenced 18C, corresponds to the longitudinal edge 13C of the distal end part 13. A second edge 18D of this triangular shape, facing the tips 15, presents a hollowed profile, corresponding approximately to an arc of circle C centred at a point O located in the vicinity of tips 15, while ua third edge 18E presents a convex profile.

The use of the retractor 10 will be described hereinafter, essentially with reference to FIGS. 5 to 8.

Figure 5:
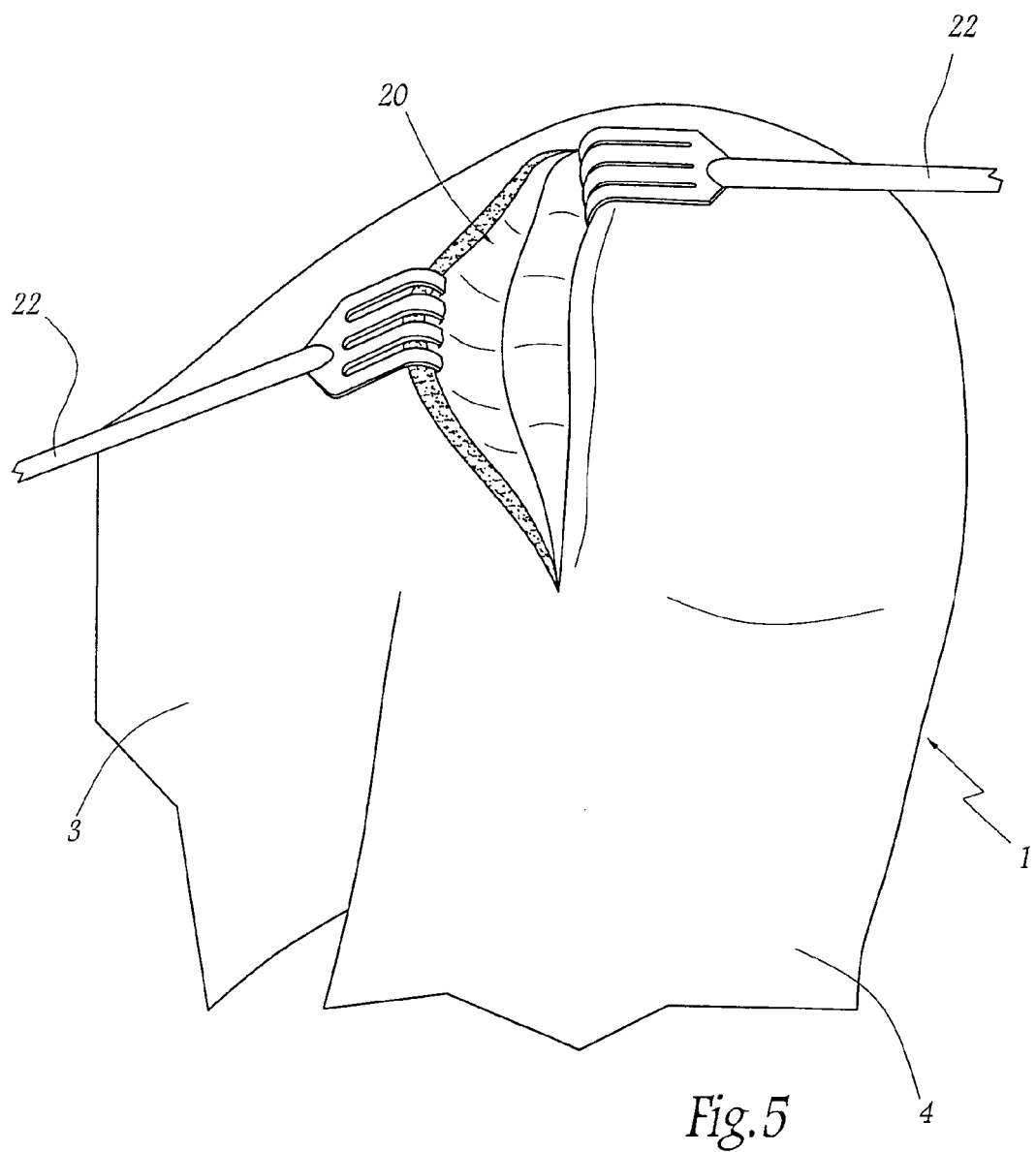
FIGS. 5 to 8 are views in perspective illustrating successive steps of the method of surgical procedure according to the invention.
Figure 6:
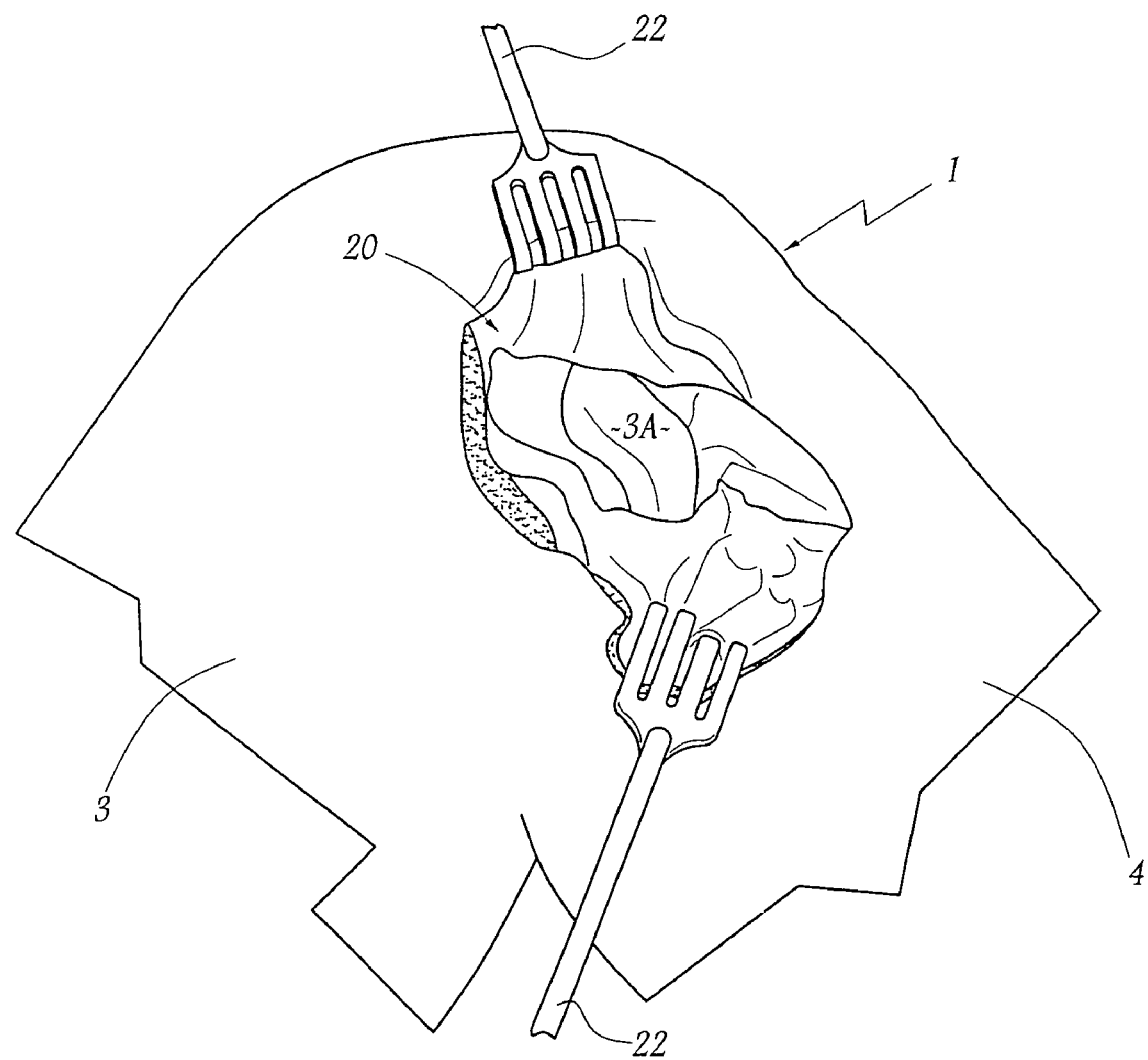
Figure 7:
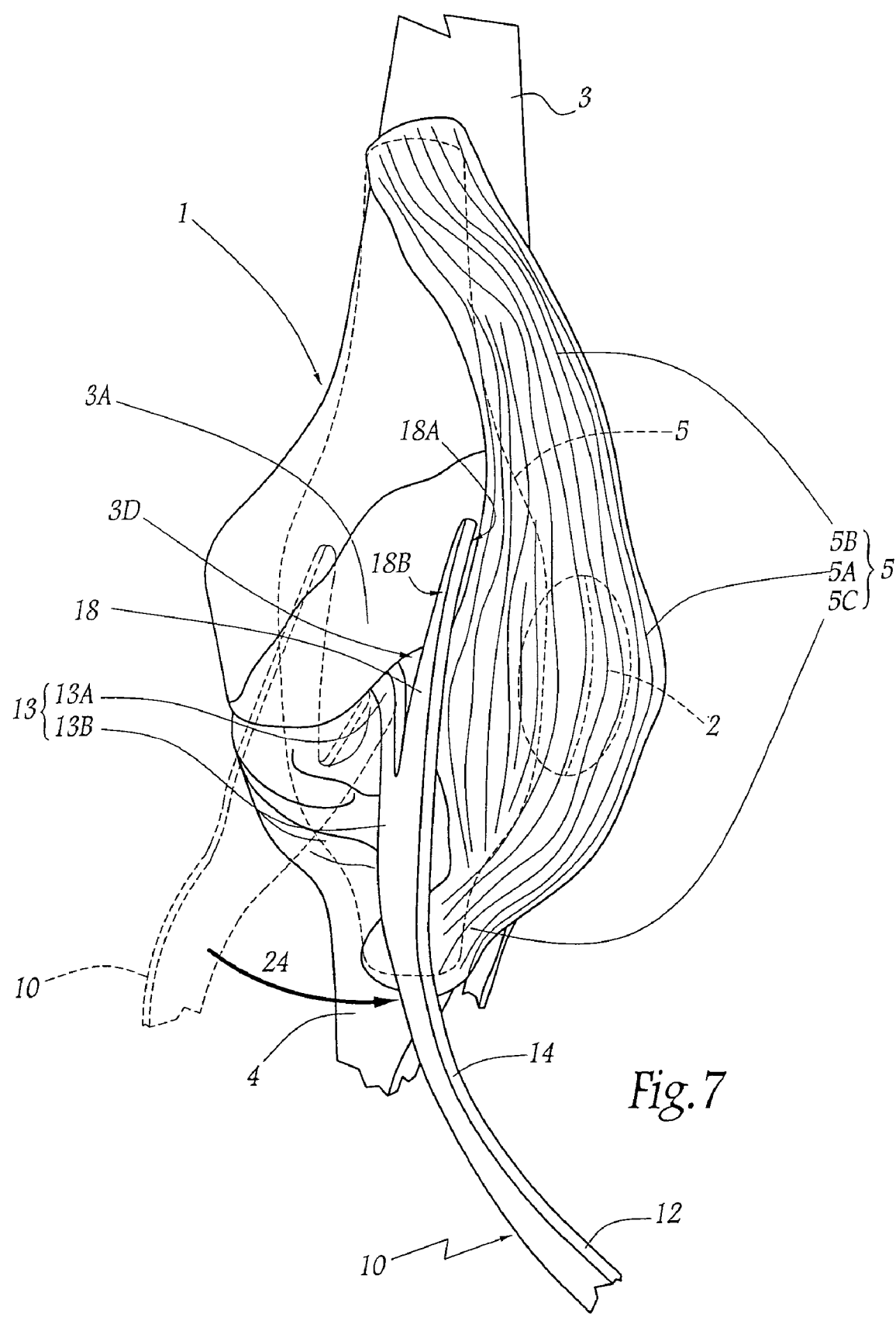
Figure 8:
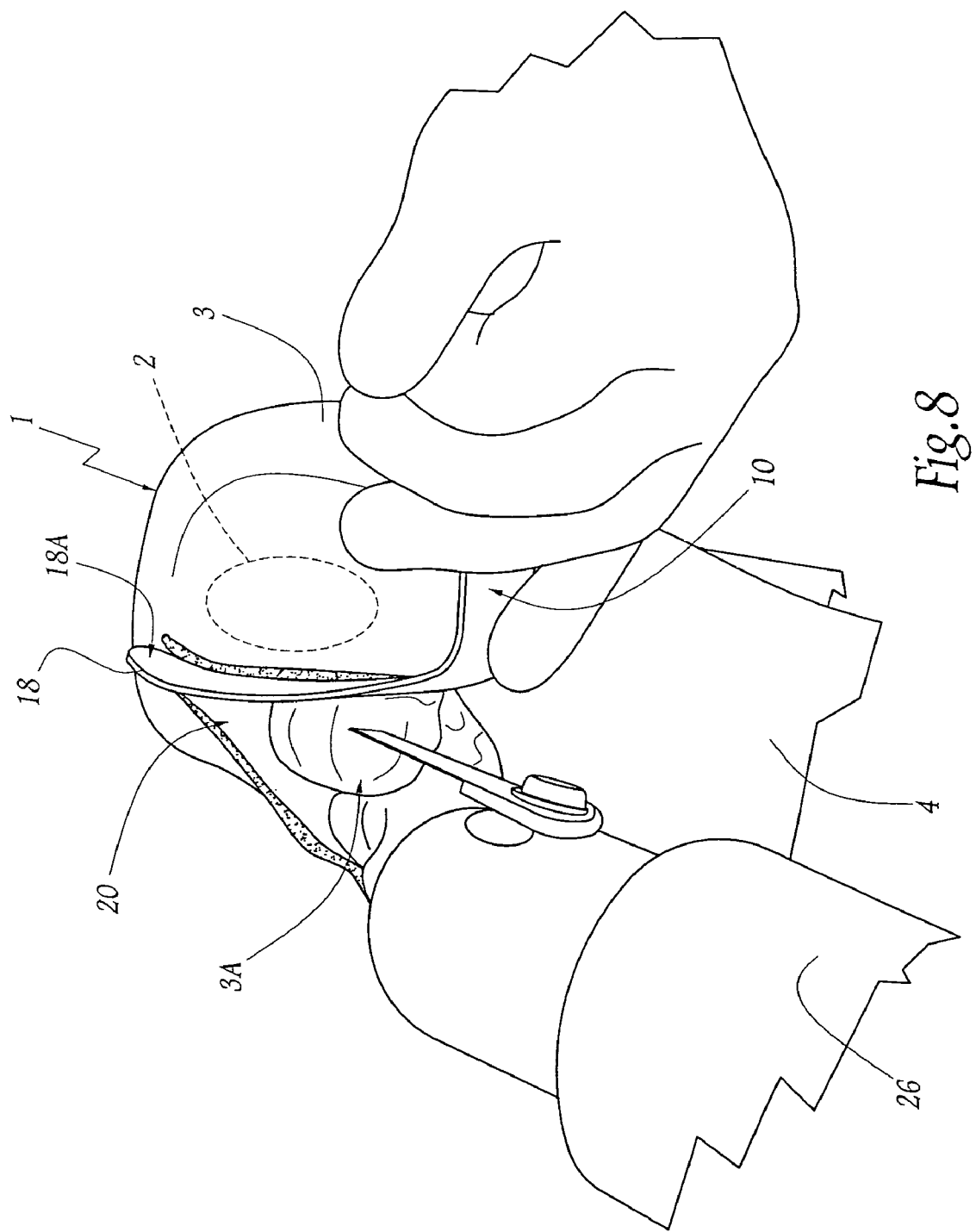

In FIG. 5, it is considered that the knee shown corresponds to the knee 1 of FIG. 1, it being noted that, contrary to FIGS. 1 and 7, in which none of the soft parts of the knee, except for the tendon of the quadriceps muscle 5, have been shown for reasons of visibility, the flap of outer skin as well as all the surrounding soft parts of the knee are shown in FIG. 5, as well as in FIGS. 6 and 8.

The surgical procedure described hereinafter aims at implanting a unicompartmental knee prosthesis at the level of the external compartment of the right-hand knee 1. To that end, as shown in FIG. 5, the surgeon places the knee in configuration of flexion, then incises the soft parts of the right-hand compartment of the knee from the front. The edges of the incision 20, made substantially vertically, are held back by surgical claws 22.

The incision and retraction of the soft parts of the right-hand compartment of the knee 1 are continued until the external condyle 3A of the femur 3 is rendered accessible to the surgeon by a globally antero-posterior surgical approach, as represented in FIG. 6.

Without incising the soft parts of the knee further, the surgeon manipulates the patellar retractor 10, gripping it at its proximal end part 12. To that end, the surgeon introduces the terminal zone 13A of the distal end part 13 of the retractor 10 in the knee 1, sliding the concave face of its pointed terminal zone 13A against the front wall of the external condyle 3A in the direction of the intercondylar space 3D. The concavity of the pointed terminal zone 13A facilitates the positioning and advance of the retractor 10 along the external condyle 3A, firstly on its front face then on its intercondylar face $3A_1$. The body 11 of the retractor 10 is thus manipulated so that the wing 18 extends at a distance from the outer flank of the tendon of the quadriceps muscle 5, as represented in broken lines in FIG. 7. In this configuration, the concave frontal face 18A is turned towards the outer flank of the current part 5A of the tendon of the quadriceps muscle 5 likewise represented in broken lines, while the opposite convex face 18B is turned towards the external condyle 3A.

The distal end part 13 is thus introduced until its tips 15 are received in the intercondylar space 3D. The length $L_D$ of the distal end of the part 13, between the tips 15 and the joint between the edges 18C and 18D of the wing 18, is provided to guarantee to the surgeon that the tips 15 have attained a sufficient depth in the intercondylar space 3D when the second edge 18D of the wing 18 is in the immediate proximity, or even substantially in contact with the soft parts adjacent the condyle 3A.

As indicated by arrow 24 in FIG. 7, the surgeon then moves the retractor 10, still manipulating it at the level of the proximal end part 12, in a tipping movement in a globally horizontal plane, centred on the intercondylar space 3D. More precisely, when the retractor 10 is being tipped, the tips 15 come into abutment against the wall $3A_1$ of the external condyle 3, as shown in FIG. 4, forming stable and resistant points of abutment. The concave face 18A of the wing 18 is then brought into contact against the outer flank of the current part 5A of the tendon of the quadriceps muscle 5, then pushes the current part 5A laterally towards the inside, until the tendon is brought into its offset position shown in FIG. 7. The retractor 10 is thus used in the manner of a lever for tipping the tendon 5. By complementarity of shapes between the face 18A and the outer flank of the tendon 5, the effort of drive of the tendon 5 is distributed over substantially the whole length of the current part 5A, in other words over the length of the tendon 5 at the level of which the patella 2 is located, without the wing 18 coming into pressing contact with the femoral epiphysis since its second edge 18D is arcuate in centred manner on the intercondylar space. The patella is thus reclined.

As the tipping is globally centred on the intercondylar space 3D, the patella 2 slides over the anterior face of the epiphysis of the femur 3, passing from its sagittal position in broken lines in FIG. 7, in which it is received in the femoral trochlea 3C, to a position offset inwardly, without, however, being completely turned round since the posterior face of the patella 2 remains directed towards the femur 3.

In its reclined configuration, the patella 2 and the corresponding current part 5A of the tendon 5 clears an antero-posterior access to the whole of the external condyle 3A, as shown in FIG. 8. the external condyle 3A is then completely exposed to the surgeon who, by means of appropriate ancillary tools, such as a saw 26 or the like, effects one or more surgical actions necessary for the implantation of the unicompartmental prosthesis at the level of the external condyle 3A. During these actions, the wing 18 protects the patella 2, particularly using its convex edge 18E.

In this way, the patellar retractor 10 is an ancillary tool that is easy to manipulate and particularly efficient for holding back the current part 5A of the quadriceps muscle tendon 5, without subjecting the latter to excessive strains.

The retractor 10 is easy to manufacture, for example from a substantially planar piece, and machined to present the tips 15 and the wing 18, which is subsequently curved to give the retractor 10 its definitive curvatures.

It will be understood that the patellar retractor 10 described hereinabove is specifically intended to recline the patella 2 during a surgical procedure at the level of the external condyle of a knee. If it is desired to operate at the level of the internal condyle, for example condyle 3B for the knee 1, another patellar retractor should be used, presenting arrangements similar to the retractor 10 and obtained by symmetry of the retractor 10 with respect to the plane P indicated in FIG. 1, which, for the retractor 10 in service, corresponds to a sagittal plane of the knee.

FIG. 9 shows a variant embodiment of the patellar retractor 10, which differs from that of the preceding Figures only by the additional presence of a second lateral wing 30 located on the longitudinal side opposite that from which the wing 18 extends. The wing 30 thus extends in projection from the body 1 from the lower longitudinal edge 13D of the part 13. This additional wing 30 presents arrangements similar to those of the wing 18, particularly concerning its curvature, with the result that the wing 30 makes it possible, when the retractor is driven in the manner of a lever described hereinabove, to push the lower end 5C of the tendon of the quadriceps muscle 5 in a medial-lateral direction.

Various arrangements and variants of the patellar retractors, and of the method of surgical procedure described hereinabove, may, in addition, be envisaged. By way of example, the proximal end part 12 of the retractor may be equipped with an added handle, presenting in particular a crest/trough profile in order to facilitate manual gripping thereof by the surgeon.

What is claimed is:

1. A method of performing a surgical procedure on a knee comprising the following successive steps of:
    Incising an anterior zone and one of an external or internal zone of the knee to form an incision;
    holding back edges of the incision to reveal at least part of a corresponding external or internal femoral condyle of the knee;
    introducing a pointed distal end of a patellar retractor into a femoral intercondylar space of the knee through the incision;
    abutting the pointed distal end on a wall of the revealed condyle facing the femoral intercondylar space; and
    pushing part of a quadriceps muscle tendon containing the patella in a medial-lateral direction towards the unrevealed condyle to dislocate a patella of the knee using the patellar retractor as a lever.

2. The method of claim 1, wherein the patellar retractor includes an elongated body having a distal end part provided with at least one terminal tip for abutment on a femoral condylar wall and a wing extending laterally in projection from the distal end part to form a frontal surface for thrusting the part of the quadriceps muscle tendon containing the patella when the tip is in abutment in the femoral intercondylar space.

3. The method of claim 1, wherein introducing the pointed end of the patellar retractor in the femoral intercondylar space comprises sliding the pointed end successively against a front wall of the revealed condyle and a wall turned towards the femoral intercondylar space of the revealed condyle.

4. The method of claim 1, wherein pushing the part of the quadriceps muscle tendon containing the patella comprises sliding the patella laterally on an anterior face of a lower epiphysis of a femur of the knee.

5. The method of claim 1, wherein pushing the part of the quadriceps muscle tendon containing the patella comprises maintaining a posterior face of the patella directed towards a femur of the knee.

6. A method of implanting a knee prosthesis comprising:
    incising a front part of a knee to form an incision to reveal at least part of a femoral condyle;
    introducing a distal end of a patellar retractor into a femoral intercondylar space of the knee through the incision, wherein the distal end of the patellar retractor includes a surface portion and a tip portion;
    abutting the tip portion of the distal end on a wall of the femoral condyle facing the femoral incondylar space to form a resistant point of abutment;
    contacting the surface portion of the distal end against a tendon of a quadriceps muscle;
    pushing part of the quadriceps muscle tendon with the patellar retractor to recline a patella of the knee; and
    implanting a prosthesis within the incision.

7. The method of claim 6, further comprising preparing the femoral condyle for implantation.

8. The method of claim 7, further comprising implanting a prosthesis at the femoral condyle.

* * * * *